(12) United States Patent
Linsi

(10) Patent No.: US 9,028,514 B2
(45) Date of Patent: May 12, 2015

(54) SURGICAL PROBE

(71) Applicant: Alcon Research, Ltd., Fort Worth, TX (US)

(72) Inventor: Thomas Linsi, Schaffhausen (CH)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 14/151,922

(22) Filed: Jan. 10, 2014

(65) Prior Publication Data

US 2014/0124476 A1     May 8, 2014

Related U.S. Application Data

(60) Division of application No. 13/900,160, filed on May 22, 2013, which is a continuation of application No. 13/010,966, filed on Jan. 21, 2011, now Pat. No. 8,475,479.

(51) Int. Cl.
| | |
|---|---|
| *A61B 17/32* | (2006.01) |
| *A61F 9/007* | (2006.01) |
| *A61B 17/3201* | (2006.01) |
| *A61B 17/29* | (2006.01) |
| *A61B 17/30* | (2006.01) |
| *A61B 17/00* | (2006.01) |

(52) U.S. Cl.
CPC ............. *A61F 9/007* (2013.01); *A61B 17/3201* (2013.01); *A61B 2017/2918* (2013.01); *A61B 2017/305* (2013.01); *A61F 9/00736* (2013.01); *A61B 2017/00526* (2013.01)

(58) Field of Classification Search
CPC ................... A61B 17/3201; A61B 2017/2918; A61F 9/007
USPC ............. 606/167, 169, 170, 171; 30/342, 329
See application file for complete search history.

(56) References Cited

U.S. PATENT DOCUMENTS

| | | | |
|---|---|---|---|
| 4,258,716 A * | 3/1981 | Sutherland | .................... 606/170 |
| 4,611,400 A | 9/1986 | Drake | |
| 4,674,501 A | 6/1987 | Greenberg | |
| 4,877,026 A | 10/1989 | De Laforcade | |

(Continued)

FOREIGN PATENT DOCUMENTS

WO     2012099641 A1     7/2012

OTHER PUBLICATIONS

International Searching Authority, International Search Report, PCT/US2011/062621, Mar. 12, 2012, 2 pages.

(Continued)

*Primary Examiner* — Victor Nguyen

(57) ABSTRACT

An exemplary surgical probe and methods of making the same are disclosed. An exemplary surgical probe may include a tubular body and a scissor assembly received at least partially within the body. The scissor assembly may include a first blade fixed to the tubular body that includes a body portion and an end portion. The scissor assembly may further include a second blade that is configured to move longitudinally within the tubular body. The body portions of the first and second blades may each define respective cross sections normal to a longitudinal axis of the tubular body. The cross sections may each define centrally disposed edges adjacent one another, and the cross sections may each be asymmetrical about a line substantially parallel to the centrally disposed edges.

7 Claims, 5 Drawing Sheets

(56) References Cited

U.S. PATENT DOCUMENTS

| | | | |
|---|---|---|---|
| 5,314,440 A | * | 5/1994 | Shapiro ........................ 359/676 |
| 5,562,693 A | | 10/1996 | Devlin et al. |
| 5,579,583 A | | 12/1996 | Mehregany et al. |
| 5,730,749 A | | 3/1998 | Battenfield |
| 2003/0120305 A1 | | 6/2003 | Jud et al. |
| 2009/0131961 A1 | | 5/2009 | Keller |

OTHER PUBLICATIONS

International Searching Authority, Written Opinion of the International Searching Authority, PCT/US2011/062621, Mar. 12, 2012, 5 pages.

European Patent Office, European Search Report, Application No. 11855924.4, Publication No. 2635209, Published Sep. 11, 2013, 4 pages.

* cited by examiner

SURGICAL PROBE

This application is a divisional of U.S. patent application Ser. No. 13/900,160 filed on May 22, 2013, which is a continuation of U.S. patent application Ser. No. 13/010,966 filed on Jan. 21, 2011.

BACKGROUND

Many microsurgical procedures require precision cutting and/or removal of various body tissues. For example, vitreoretinal surgery often requires the cutting, removal, dissection, delamination, coagulation, or other manipulation of delicate tissues such as the vitreous humor, traction bands, membranes, or the retina. The vitreous humor, or vitreous, is composed of numerous microscopic fibers that are often attached to the retina. Therefore, cutting, removal, or other manipulation of the vitreous must be done with great care to avoid traction on the retina, the separation of the retina from the choroid, a retinal tear, or, in the worst case, cutting and removal of the retina itself.

Microsurgical instruments, such as vitrectomy probes, fiber optic illuminators, infusion cannulas, aspiration probes, scissors, forceps, and lasers are typically utilized during vitreoretinal surgery. These devices are generally inserted through one or more surgical incisions in the sclera near the pars plana, which are called sclerotomies. One exemplary surgical probe includes a cutting blade disposed within a tubular probe needle. The cutting blade moves reciprocally within the probe needle relative to a second blade that is fixed within the tubular needle. The moving blade cuts material, e.g., vitreous humor, in a scissor-like motion adjacent the fixed blade.

To reduce potential damage to surgical sites and reduce recovery time, the size of the surgical incisions must be kept to a minimum. Accordingly, surgical probes are being designed in progressively smaller sizes to facilitate correspondingly smaller surgical incisions. As probe size decreases, cutting blades within the probes are decreased in size as well, thereby reducing blade strength and increasing the risk of fatigue or failure. Further, known mechanical forming methodologies such as grinding or machining are impractical at the small sizes typical of the blades, which typically have a maximum cross-sectional width of less than one (1) millimeter. Additionally, known forming processes are generally limited to blades having cross sections defining rectangular shapes, which prevents widening the blades to increase strength. Accordingly, current manufacturing methodologies and blade strength inhibit the degree to which probe needles may desirably be further reduced in size.

BRIEF DESCRIPTION OF THE DRAWINGS

While the claims are not limited to the illustrated examples, an appreciation of various aspects is best gained through a discussion of various examples thereof. Referring now to the drawings, illustrative examples are shown in detail. Although the drawings represent the various examples, the drawings are not necessarily to scale and certain features may be exaggerated to better illustrate and explain an innovative aspect of an example. Further, the examples described herein are not intended to be exhaustive or otherwise limiting or restricting to the precise form and configuration shown in the drawings and disclosed in the following detailed description. Exemplary illustrations of the present invention are described in detail by referring to the drawings as follows.

DETAILED DESCRIPTION

Various exemplary illustrations are described herein of a surgical probe and methods of making the same. An exemplary surgical probe may include a tubular body defining a cutting aperture at a first end of the body. The surgical probe may further include a scissor assembly received at least partially within the body and extending along a longitudinal axis of the body. The scissor assembly may further include a first blade fixed to the tubular body that includes a body portion and an end portion. The scissor assembly may further include a second blade that is configured to move longitudinally within the tubular body. The second blade may also include a body portion and a cutting edge at an end of the body portion. The cutting edge may be configured to cut material, e.g., against the end portion of the first blade. The body portions of the first and second blades may each define respective cross sections normal to a longitudinal axis of the tubular body. The cross sections may each define centrally disposed edges adjacent one another, and the cross sections may each be asymmetrical about a line substantially parallel to the centrally disposed edges. As will be described further below, the asymmetrical cross-sections may allow an enlarged section modulus of the blade body portions, thereby increasing overall strength of the blades.

Exemplary methods of forming a surgical probe may include forming first and second blades that include elongated body portions. The first blade may include an end portion, adjacent which a cutting edge of the second blade may initiate a scissor cutting motion. The exemplary methods may further include establishing the body portions of the first and second blades as defining asymmetrical cross sections normal to the elongated body portions of the blades, relative to a line substantially parallel to centrally disposed edges of the cross sections. The method may further include inserting the first and second blades into a tubular body having a cutting aperture at a first end of the tubular of the body, and fixing the first blade to the tubular body. The second blade may be configured to translate longitudinally within the tubular body.

Figure 1A:
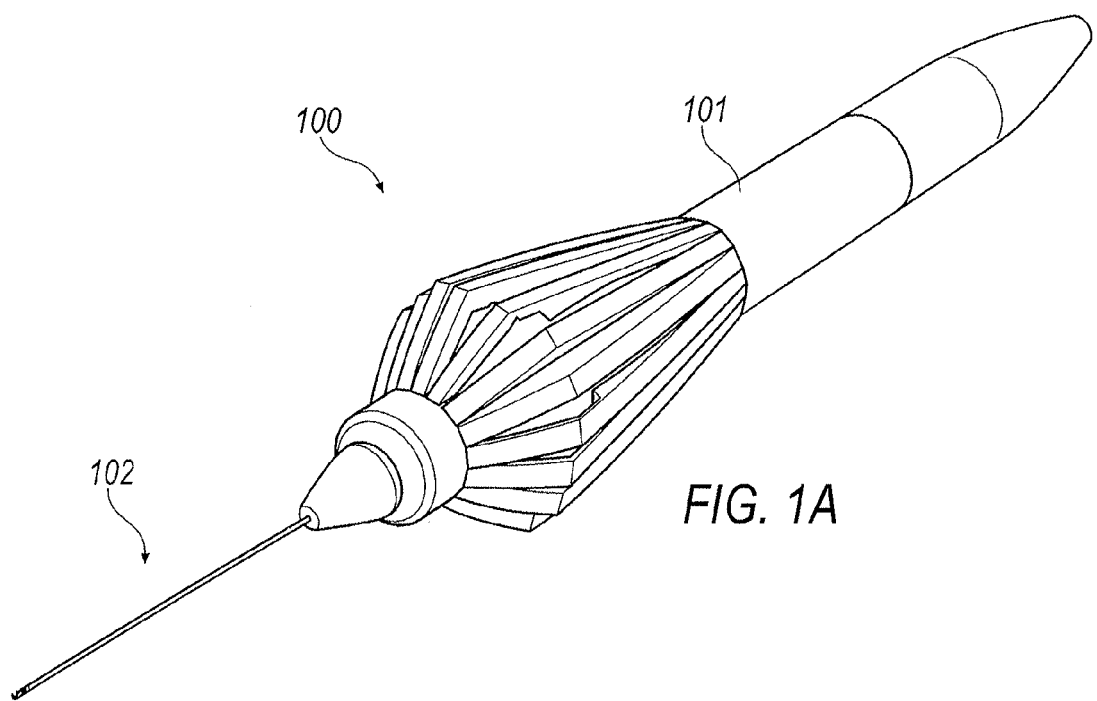
FIG. 1A illustrates a perspective view of an exemplary surgical probe.
Figure 1B:
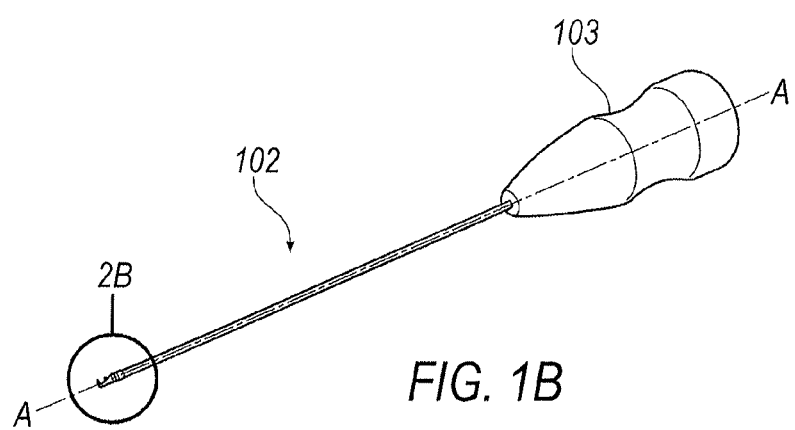
FIG. 1B illustrates a perspective view of a tubular body and scissor assembly of the surgical probe of FIG. 1A.

Turning now to FIGS. 1A and 1B, an exemplary probe 100 is illustrated. A surgical probe 100 may include any ophthalmic surgery probe. For example, probe 100 may be a vertical scissor probe, as shown throughout the figures and described below. The surgical probe 100 may include a handle 101 that allows manipulation, e.g., by a surgeon, of a tubular body 102 secured to the handle 101. The tubular body 102 may be configured to be inserted into a surgical incision, e.g., during various posterior and anterior ophthalmic surgical procedures such as Proliferative Vitreoretinopathy (PVR) and pediatric Retinopathy of Prematurity (ROP), merely as examples. Additionally, as best seen in FIG. 1B, the tubular body 102 may be selectively secured to the handle 101 via a connector 103 that facilitates removal and/or replacement of the tubular body 102. The tubular body 102 may define a longitudinally extending axis A-A.

Figure 2A:
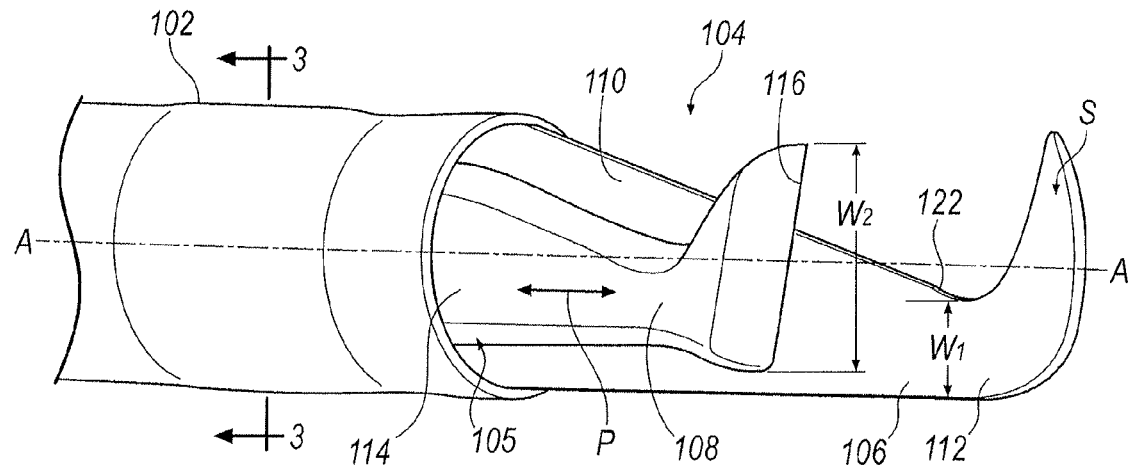
FIG. 2A illustrates an enlarged perspective view of the exemplary surgical probe of FIGS. 1A and 1B.
Figure 2B:
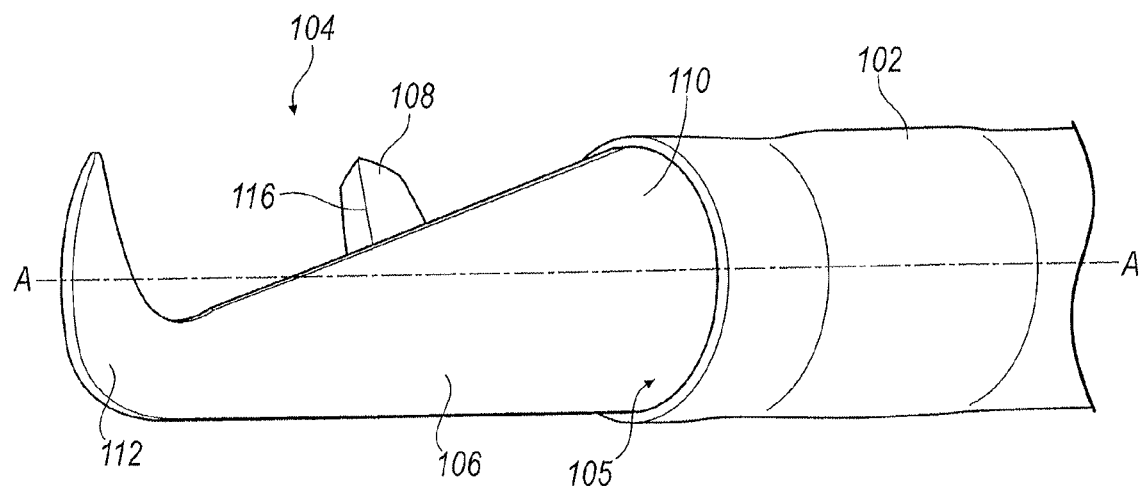
FIG. 2B illustrates an enlarged perspective view of the exemplary surgical probe of FIGS. 1A and 1B, taken from an opposite side of the probe compared with FIG. 2A.

Turning now to FIGS. 2A and 2B, the probe 100 may include a scissor assembly 104 that is received at least partially within the tubular body 102 and extends along the longitudinally axis A-A. The scissor assembly 104 may include first and second blades 106, 108. The first blade 106 may be fixed relative to the tubular body 102, e.g., by welding. The first blade may include a body portion 110 and an end portion 112. The second blade 108 may be configured to move longitudinally within the tubular body 102 relative to the first blade 106 along a cutting path P. The second blade may include a body portion 114 and a cutting edge 116 at an end of the body portion 114. The cutting edge 116 may be generally configured to cut material adjacent or against the end portion 112 of the first blade 106. More specifically, the cutting edge 116 may generally cut material in a scissor-like motion, in cooperation with the end portion 112 of the first blade 106.

As best seen in FIGS. 2A and 2B, the first blade 106 may include a relatively thin neck portion 122 between the end portion 112 and body portion 110. The end portion 112 may thereby define a generally "hooked" shape extending laterally, e.g., relative to the axis A-A. The thin neck portion 122 generally facilitates movement of the second blade 108 relative to the first blade 106, while allowing a cutting surface S that allows full engagement of the cutting edge 116. More specifically, the neck portion 122 defines a lateral width $W_1$ that is smaller than a lateral width $W_2$ of the cutting edge 116. Any wear, e.g., as caused by friction between the cutting edge 116 and the first blade 106, may be thereby reduced while allowing a relatively larger width of the cutting edge 116 to be applied to the material (not shown) to be cut.

Figure 3A:
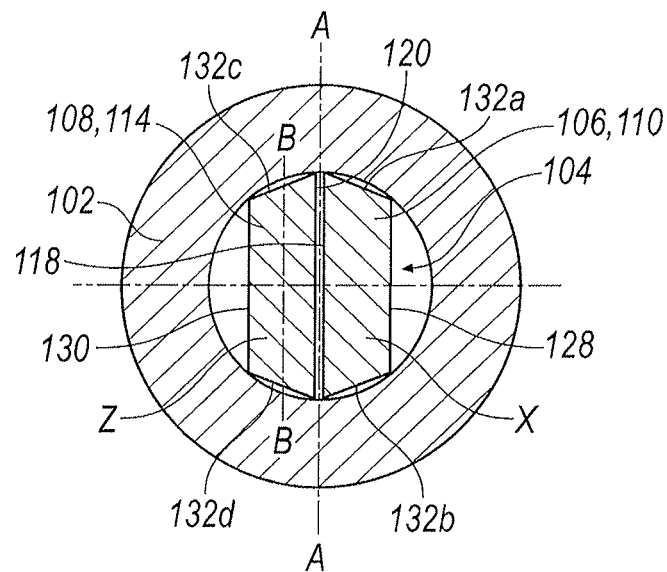
FIG. 3A illustrates a cross sectional view of an exemplary surgical probe.

Turning now to FIG. 3A, which is a cross sectional view of the tubular body 102 and scissor assembly 104, the scissor assembly 104 is illustrated in further detail. More specifically, FIG. 3A illustrates a cross sectional view of the body portions 110, 114 of the first blade 106 and second blade 108, respectively. As shown in FIG. 3A, the cross sections of the body portions 110, 114 as viewed normal to the longitudinally axis A-A of the tubular body 102 each define centrally disposed edges 118 and 120 that are generally adjacent one another. Further, each of the cross sections X and Z of the first and second blades 106 and 108 are generally asymmetrical with respect to a line B-B that is substantially parallel to the centrally disposed edges 118, 120. As will be described further below, the asymmetrical cross sections X and Z may facilitate an enlarged section modulus compared with blades having a quadrangular-shaped section.

The cross sections X and Z may be substantially defined by the centrally disposed edges 118, 120, distal edges 128, 130 and lateral edges 132 extending therebetween. More specifically, cross section X of the second blade 108 is generally defined by the edges 118, 132c, 132d, and 130, while cross section Z of first blade 106 is defined by edges 120, 132a, 132b, and 128. The centrally disposed edges 118 and 120 may each extend across substantially the entire inner diameter of the tubular body 102, and may each be the same general size and cross sectional shape. Alternatively, the blades 106, 108 may be different sizes, e.g., where first blade 106 is enlarged for a more secure positioning within the tubular body 102.

The distal edges 132 of each cross section X and Z are relatively smaller in extent across the opening defined by the tubular body 102 compared with the centrally disposed edges 118, 120. Accordingly, the cross sections X and Z may define a generally trapezoidal shape. As will be explained further below, the generally trapezoidal shape and/or asymmetrical shape defined by the cross sections X and Z of the body portions 110 and 114 of the first and second blades 106 and 106 may be generally formed in an etching process.

Figure 3B:
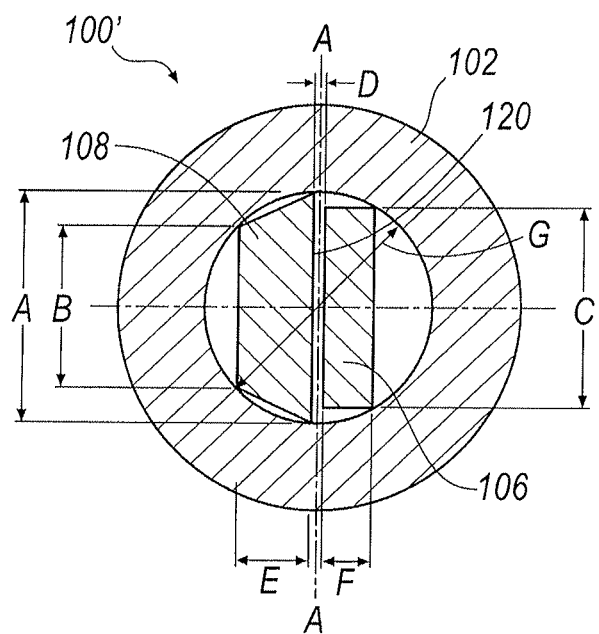
FIG. 3B illustrates a cross sectional view of another exemplary surgical probe.

Turning now to FIG. 3B, a cross-sectional view of another exemplary probe 100' is illustrated. As with probe 100 described above, the probe' 100 included first and second blades 106, 108 received within tubular body 102. However, first blade 106 defines a generally symmetrical and/or rectangular cross-section, while the second blade 108 defines a generally asymmetrical and/or trapezoidal cross-section. Alternatively, the first and second blades 106, 108 may each define an asymmetrical and/or trapezoidal cross-section, e.g., as described above in regard to probe 100. While one of the first and second blades 106, 108 is fixed with respect to the tubular body 102, the other may be movable to allow axial translation with respect to the tubular body 102.

The generally asymmetrical/trapezoidal cross-section of blade 108 may generally have an increased section modulus, and thereby provide greater strength, compared with the generally symmetrical/rectangular blade 106. Although only one of the blades 106, 108 shown in FIG. 3B has an asymmetrical/trapezoidal cross-section, the exemplary illustration in FIG. 3B is also generally illustrative of the improved strength of an asymmetrical/trapezoidal cross-section compared with a symmetrical/rectangular cross section.

In one exemplary illustration, the tubular body 102 shown in FIG. 3B is provided in a 23-gauge size having an inner diameter G of 0.45 millimeters. The asymmetrical or trapezoidal shape may facilitate an enlarged section and/or an increased section modulus of the blade 108, thereby increasing strength of the asymmetrical/trapezoidal blade 108 compared with symmetrical/rectangular blade 106. The blades 106, 108 are spaced apart by a small gap D of 0.01 millimeters. One known blade 106 has a rectangular cross section defining a maximum width C of 0.38 millimeters and a maximum thickness F of 0.1 millimeters, resulting in a cross sectional area of 0.038 millimeters$^2$ and a section modulus, $W_y$, of 0.000633 millimeters$^3$. By contrast, the asymmetrical shape of blade 108 allows for an increased length A of the centrally disposed edge 120, which extends 0.44 millimeters, due to the sloped configuration of the lateral edges 132 that create the trapezoidal and/or asymmetrical shape. Further, the thickness E of the blade 108 is increased to 0.15 millimeters, which is also facilitated by the sloped lateral edges 132. Additionally, the distal edge defines a width B of 0.3 millimeters. Accordingly, the cross-sectional area of the generally trapezoidal blade 108 is increased to 0.056 millimeters$^2$. Further, the section modulus, $W_y$, is also increased to 0.00129 millimeters$^3$. Accordingly, the trapezoidal and/or asymmetrical shape of the blade 108 results in an increased strength of the blade 108 compared with blades having a traditional rectangular-shaped section, e.g., blade 106.

In another exemplary illustration, a 29-gauge size tubular body has an inner diameter of 0.2 millimeters. The blades 106, 108 are spaced apart by a small gap D of 0.004 millimeters. This exemplary illustration of the blade 106 has a rectangular cross section defining a maximum width C of 0.16 millimeters and a maximum thickness F of 0.04 millimeters, resulting in a cross sectional area of 0.0064 millimeters$^2$ and a section modulus, $W_y$, of 0.00004267 millimeters$^3$. By contrast, an asymmetrical shape such as that shown for blade 108 allows for an increased length A of the centrally disposed edge 120, which extends 0.19 millimeters, due to the sloped configuration of the lateral edges 132 that create the trapezoidal and/or asymmetrical shape. Further, the thickness E of the blade 108 is increased to 0.07 millimeters, which is also facilitated by the sloped lateral edges 132. Additionally, the distal edge defines a width B of 0.13 millimeters. Accordingly, the cross-sectional area of the blade 108 is increased to 0.0112 millimeters$^2$. Further, the section modulus, $W_y$, is also increased to 0.000122 millimeters$^3$. Accordingly, the trapezoidal and/or asymmetrical shape of the blade 108 results in an increased strength of the blade 108 compared with blades having a traditional rectangular-shaped section, e.g., blade 106.

The above dimensions are provided merely as an exemplary illustration of the potential for increased strength of the blades 106, 108 that may result from the asymmetrical and/or trapezoidal cross-sectional shape. Accordingly, any other dimensions may be employed for blades 106, 108 that are convenient.

Figure 4:
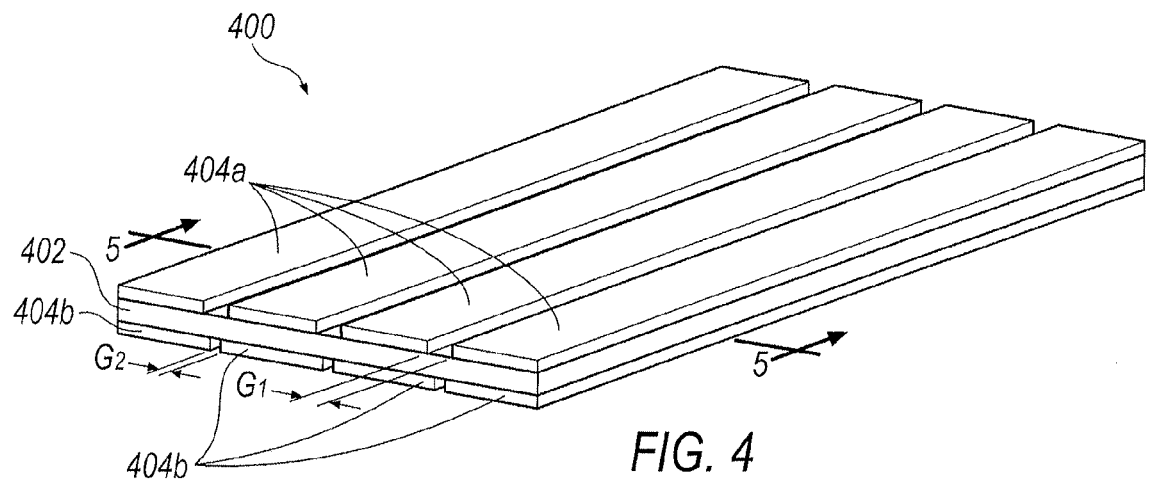
FIG. 4 illustrates a perspective view of an exemplary blade sheet used to produce blades for a surgical probe.

Turning now to FIG. 4, an exemplary blade sheet assembly 400 used to form a plurality of blades 106 and/or 108 is illustrated. Blade sheet 400 generally includes a sheet blank 402 from which a series of blades 106 and/or 108 may be formed, in any manner that is convenient.

In one exemplary illustration, blades 106, 108 are formed in an etching process applied to the blade sheet assembly 400. An etching process may be advantageous as compared with other mechanical forming processes where the blades 106, 108 are very small, such that machining or grinding is impractical. Accordingly, blade sheet assembly 400 may include an inert substance or generally etch resistant substance 404 applied to the sheet blank 402. For example, as shown in FIG. 4, a series of etch resistant strips 404a, 404b may be applied to opposing sides of the sheet material 402. Further, gaps $G_1$ between the strips 404a may be generally larger than gaps $G_2$ between the strips 404b. Accordingly, when an etching material is placed in the vicinity of the gaps, the etching material acts upon the exposed areas and produces the substantially trapezoidal shape exhibited by the cross sections X and Z of the first and second blades 106 and 108.

Figure 5:
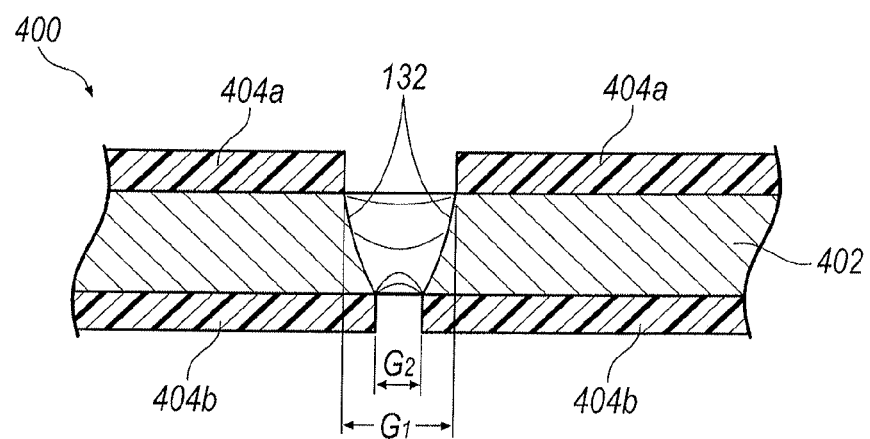
FIG. 5 illustrates a cross sectional view of the exemplary blade sheet of FIG. 4.

More specifically, as best illustrated in FIG. 5, the etch resistant material 404a defines a large gap $G_1$ between each strip. By contrast, etch resistant strips 404b define a smaller gap $G_2$ between each strip that restricts the surface area acted upon by the etching material. Accordingly, the etching material applied on the side of the blade sheet assembly 400 adjacent strips 404a etches away larger widths of the sheet material 402 than the etching material applied adjacent strips 404b, thereby creating an inclined etched surface which forms the lateral edges 132 of the blades 106, 108. The different sized gaps thus define the generally trapezoidal shape and/or asymmetrical cross sectional shape of the blades 106, 108.

Figure 6:
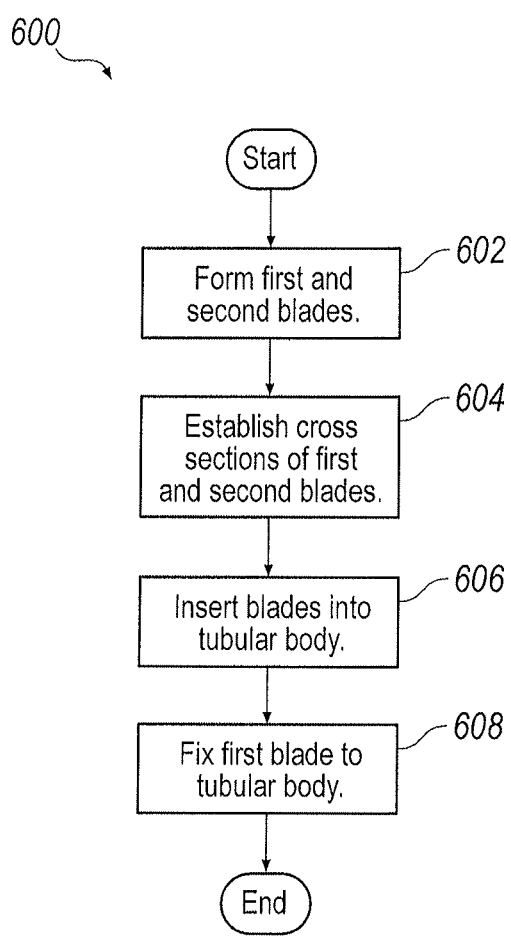
FIG. 6 illustrates a process flow diagram of an exemplary method of forming a surgical probe.

Referring now to FIG. 6, an exemplary process 600 for forming a surgical probe 100 is described. Process 600 may begin at block 602, where first and second blades are formed. For example, as described above, a first blade 106 having an elongated body portion 110 and an end portion 112 may be formed, e.g., in an etching process as described above. Further, a second blade may be formed including an elongated body portion 114 and a cutting edge 116 at an end of the body portion 114. Process 600 may then proceed to block 604.

At block 604, the body portions of the first and second blades may be established as defining asymmetrical cross sections. For example, as described above, the body portions 110 and 114 may each generally define a trapezoidal, or otherwise asymmetrical, cross sectional shape about a line B-B that is substantially parallel to the centrally disposed edges 118 and 120 of the cross sections X and Z. Further, as described above the generally asymmetrical cross sectional shape may be created in an etching process applied to a sheet material 402. Further, this may occur during an etching process used to form the blades, e.g., as described above in block 602. An etch-resistant material 404 may be secured to the opposing surfaces of the blade sheet 400 in strips 404a, 404b. After the etch resistant material 404 is applied to the sheet material 402, an etching material may be applied to exposed areas of the sheet material 402. More specifically, the etching material may generally work within gaps $G_1$ and $G_2$ on opposing sides of the sheet material 402. Furthermore, the different sized gaps $G_1$ and $G_2$ may allow exposure of different widths of the sheet material 402, thereby forming the asymmetrical and/or generally trapezoidal cross sectional shape of the body portions 110 and 114. The cross sectional areas of each of the body portions 110 and 114 may, in some exemplary illustrations, be substantially equal.

Various features of the blades 106, 108 may also be formed, such as the cutting edge 116 of the second blade 108 and the generally hooked-shape end portion 112 of the first blade 106. The cutting edge 116 may be formed in any process that is convenient, e.g., a grinding process. The end portion 112, including the relatively thin neck portion 122, may be formed in an etching process, or any other forming process that is convenient. Additionally, either blade 106, 108 may be polished, e.g., to remove any relative sharp edges where they are not desired. Process 600 may then proceed to block 606.

At block 606, the first and second blades 106 and 108 may be inserted into a tubular body 102 having a cutting aperture at a first end of the tubular body. For example, as described above the blades 106, 108 may be at least partially received within the tubular body 102, with the end portion 112 and cutting edge 116 extending outside the tubular body 102 to facilitate cutting with the scissor assembly 104.

Proceeding to block 608, a first one of the blades, e.g., first blade 106, may be generally fixed to the tubular body 102. For example, the first blade 106 may be welded to the tubular body. Additionally, the second blade 108 may be configured to translate longitudinally within the tubular body 102, e.g., to generally facilitate the relative cutting motion of the first and second blades 106 and 108. Process 600 may then terminate.

Accordingly, surgical probe 100 generally allow for a tubular body 102 that is reduced in size, while providing adequate strength of the blades 106, 108 due to the asymmetrical and/or trapezoidal shape of the blades 106, 108. Further, the exemplary process 600 generally provides a robust forming process for creating the asymmetrical and/or trapezoidal shape of the blades 106, 108, even at the extremely small sizes typical of the surgical probe 100.

Reference in the specification to "one example," "an example," "one embodiment," or "an embodiment" means that a particular feature, structure, or characteristic described in connection with the example is included in at least one example. The phrase "in one example" in various places in the specification does not necessarily refer to the same example each time it appears.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary.

What is claimed is:

1. A method of forming a surgical probe, comprising:
   forming first and second blades, the first blade including an elongated body portion and an end portion, the second blade including an elongated body portion and a cutting edge at an end of the body portion, the cutting edge configured to cut material against the end portion of the first blade;
   establishing the body portions of the first and second blades as defining cross sections normal to the elongated body portions of the blades, the cross sections each defining centrally disposed edges adjacent one another, at least one of the cross sections being asymmetrical about a line substantially parallel to the centrally disposed edges;
   inserting the first and second blades into a tubular body having a cutting aperture at a first end of the tubular body; and
   fixing the first blade to the tubular body, the second blade configured to translate longitudinally within the tubular body;
   wherein forming the first and second blades includes:
   providing a sheet material having opposing surfaces;
   securing an etch-resistant material to the opposing surfaces; and
   applying an etching material to exposed areas of the sheet material.

2. The method of claim 1, wherein forming the first and second blades includes etching the sheet material to define a pair of opposing lateral edges adjacent the centrally disposed edge, wherein a first one of the opposing faces includes the centrally disposed edges, wherein a second one of the opposing faces includes a distal edge opposite the centrally disposed edge.

3. The method of claim 2, wherein securing the etch-resistant material to the opposing surfaces includes defining exposed gaps in the etch-resistant material, wherein the gaps on the second one of the opposing faces are larger than the gaps on the first one of the opposing faces.

4. The method of claim 1, further comprising establishing the at least one of the cross sections as generally trapezoidal.

5. The method of claim 1, further comprising establishing the tubular body as defining an inner diameter no greater than 0.45 millimeters (mm), and the at least one of the cross sections as having a cross-sectional area greater than 0.038 square millimeters (mm2).

6. The method of claim 5, further comprising establishing the at least one of the cross sections as having a section modulus greater than 0.000633 millimeters-cubed (mm3).

7. The method of claim 1, wherein the cross sections each define a substantially equal cross-sectional area.

* * * * *